United States Patent [19]

Kourilsky et al.

[11] Patent Number: 5,635,354
[45] Date of Patent: Jun. 3, 1997

[54] METHOD FOR DESCRIBING THE REPERTOIRES OF ANTIBODIES (AB) AND OF T-CELL RECEPTORS (TCR) OF AN INDIVIDUAL'S IMMUNE SYSTEM

[75] Inventors: Philippe Kourilsky; Christophe Pannetier, both of Paris; Madeleine Cochet, Fontenay-aux-Roses, all of France

[73] Assignees: Institut National de la Sante et de la Recherche Medicale (Inserm), Paris; Institut Pasteur, Paris Cedex, both of France

[21] Appl. No.: 435,529

[22] Filed: May 5, 1995

Related U.S. Application Data

[63] Continuation of Ser. No. 84,249, filed as PCT/FR92/00014, Jan. 9, 1992, abandoned.

[30] Foreign Application Priority Data

Jan. 9, 1991 [FR] France ................................. 91 00189

[51] Int. Cl.$^6$ ................................. C12Q 1/68; C12P 19/34
[52] U.S. Cl. ................................. 435/6; 435/91.1; 435/91.2
[58] Field of Search ................................. 435/6, 91.1, 91.2

[56] References Cited

U.S. PATENT DOCUMENTS

| | | | |
|---|---|---|---|
| 4,851,331 | 7/1989 | Vary et al. | 435/6 |
| 4,879,214 | 11/1989 | Kornher et al. | 435/6 |
| 5,126,239 | 6/1992 | Livak et al. | 435/6 |
| 5,336,598 | 8/1994 | Kotzin et al. | 435/7.24 |

OTHER PUBLICATIONS

Asarnow et al., *Nature* 341, 60–62 (1989).
Goudie, *J. Pathol.* 158, 261–265 (1989).
Brisco et al., *Brit. J. Haem.* 75, 163–167 (1990).
Takagaki et al., *Nature* 339, 712–714 (1989).
Roth et al., *Chem. Abstracts* 111, 176 (1989).
Roth et al., *BioTechniques* 7(7), 746–754 (1989).
Choi et al., *PNAS* 86, 8941–8945 (1989).
Sauvaigo et al., *Nucleic Acids Res.* 18(11), 3175–3183 (1990).
Guggenheim et al., *Endocrinology* 118(4), 1710–1715 (1986).

*Primary Examiner*—Kenneth R. Horlick
*Attorney, Agent, or Firm*—Oblon, Spivak, McClelland, Maier & Neustadt, P.C.

[57] ABSTRACT

In a method for describing repertoires of antibodies (Ab) and T cell receptors (TcR) of the immune system of an individual, reverse transcription is carried out on the mRNA contained in a biological sample, separate amplifications are then carried out on the transcription product (or directly on the DNA extracted from the sample) by a PCR type method for each primer pair V, C, where V corresponds to a variable segment of the repertoire of interest and C hybridizes on the constant segment of the repertoire of interest. For each J segment of the labelled repertoire, an elongation step is carried out on each of the amplification products using a specific oligonucleotide of this segment J as primer and the amplification product as matrix. For each elongation product corresponding to a triplet (V, C)J thus obtained, the size of the different elongation products is revealed. The description of the repertoires corresponds to a VCJ triplet and to the element size for each element of the repertoire.

10 Claims, 2 Drawing Sheets

METHOD FOR DESCRIBING THE REPERTOIRES OF ANTIBODIES (AB) AND OF T-CELL RECEPTORS (TCR) OF AN INDIVIDUAL'S IMMUNE SYSTEM

This application is a continuation of application Ser. No. 08/084,249, filed on Jul. 9, 1993, now abandoned, which was filed as International Application No. PCT/FR92/00014 filed Jan. 9, 1992.

BACKGROUND OF THE INVENTION

Field of the Invention

The present invention relates to a method which enables an individual's immune repertoire to be described, and thus certain pathological states to be detected and/or monitored.

An essential feature of the immune system is the capacity to recognize specifically a large number of antigens. In vertebrates, the T and B lymphocytes mainly execute this function of recognition, by means of at least three transmembrane molecular complexes; immunoglobulin for B cells, and the two T receptors for T lymphocytes: the $\alpha\beta$ receptor and the $\gamma\delta$ receptor, which thus define two subpopulations among the collective T lymphocytes (Wilson et al., 1988; Raulet, 1989).

To the tremendous variety of antigens to be recognized, there corresponds a very wide potential diversity of these three types of receptors. In effect, these three molecular complexes, of related structure, are composed of two (for each of the T receptors) or four (for immunoglobulins) peptide chains, the $NH_2$-terminal domains of which are highly variable. It is the existence of a strong interaction between a given antigenic determinant and the site consisting of these variable domains which constitutes the expression at molecular level of the phenomenon of recognition. Thus, the information contained in the genome of a mouse enables it to produce potentially at least $10^{11}$ immunoglobulins of different variable region, $10^{15}$ different $\alpha\beta T$ receptors and $10^{18}$ different $\gamma\delta T$ receptors.

The notion of repertoire thus emerges: the set of immunoglobulin variable regions present at a given instant in an organism constitutes the current repertoire of immunoglobulins. Similarly, the set of $\gamma\delta T$-receptor variable regions possibly capable of being produced by a mouse genome constitutes the potential repertoire of $\gamma\delta$ lymphocytes.

The immune system hence contains, in fact, three complex repertoires, since the T-receptor repertoire must be subdivided into an $\alpha\beta T$-receptor and a $\gamma\delta T$-receptor repertoire.

The mechanisms which enable the huge diversity of T- and B-lymphocyte receptors to be produced are now well known (Tonegawa, 1983). The variable region of an immunoglobulin or of a T receptor is composed of the $NH_2$-terminal domains of two peptide chains. The genes coding for these two proteins are the result of somatic rearrangements which juxtapose a V segment, one or two D segments depending on the chains, and a J segment. The number of V, D and J segments available in the different loci provides a first source of diversity, termed combinatorial diversity (see Table 1). Furthermore, the lack of precision in the junctions between two of these segments (V-D, D-D, D-J or V-J junctions) introduces a second source of diversity, termed junctional diversity, since, on the one hand each of the two juxtaposed ends can have a few bases cleaved from it, and on the other hand some nucleotides can be inserted at the joining site. Lastly, in the case of genes coding for immunoglobulins, somatic mutations can take place in the second exon of the rearranged gene, thereby constituting a third source of diversity.

Depending on the type of receptor, $\alpha\beta$, $\gamma\delta$ or immunoglobulin, each of these three sources of diversity is a greater or lesser component of the total diversity. Thus, while the number of V, D and J segments available is smallest in the case of the $\gamma\delta$ receptor, the extent of the repertoire of this receptor remains potentially very large. This essentially stems from the fact that the gene coding for the $\delta$ chain can comprise zero, one or two D elements, which can, furthermore, be read in the three reading frames, whereas the $V_H$ and $\beta$ chains possess one and only one D element. In fact, the diversity of the $\gamma\delta$-receptor repertoire may be described in the following manner: it appears that a small number of V and J segments is available, but the number of V segments of the $\delta$ chain is still not properly known, and there is a very wide potential junctional diversity which manifests itself in a large variation in the length of the second exon of the rearranged gene, especially in the case of the gene coding for the $\delta$ chain (Raulet, 1989).

The function of the $\alpha\beta T$ lymphocytes is relatively well known: they participate in cytolysis by killer cells, in reactions which regulate antibody synthesis and in inflammatory phenomena. The function of the $\gamma\delta T$ lymphocytes is still poorly understood: it is generally accepted that, apart from their probable role in the ontogeny of the immune system, the $\gamma\delta T$ cells participate in immune surveillance. As regards the various functions of antibodies, these are relatively well known and will not be restated here.

There is nothing at present capable of describing the collective antibodies and T receptors (i.e. the Ab and the TcR repertoires) expressed at a given moment in an individual. It represents a monumental task, since each of the repertoires probably contains millions of different molecules. Only a small number of reagents capable of specifically recognizing this or that element of such a repertoire is as yet available. It is, of course, possible to work more shrewdly by determining the sequence of a certain number of expressed genes. However, practical considerations make it scarcely conceivable to analyze routinely more than about ten or, perhaps, a hundred genes, and the operation is expensive and very lengthy. In short, the repertoires of antibodies and of T receptors are described at the present time only by means of a small number of parameters. Hence methods are not available which permit a rapid and effective analysis of the physiological an pathological situations associated with the statement of these repertoires. For example, it is clear that these repertoires vary during a voluntary immunization (vaccine), or during infection by pathogenic microorganisms, or during the progress of autoimmune pathologies. In the latter case, there are many reasons to believe that predisposition to these diseases mirrors a certain composition of the repertoires. It is hence very probable that a good method of analysis of the repertoires would have medical spin-offs, and could form the basis of techniques of medical analysis and of diagnosis.

A method which is now very widely used for the purpose of studying the diversity and distribution of the three repertoires, of immunoglobulins and $\alpha\beta$ and $\gamma\delta$ receptors, is that of amplification by PCR (polymerase chain reaction). This technique consists in amplifying genomic DNA or complementary DNA with a series of specific primer pairs (V,C) or (V,J) and, where appropriate, cloning and then sequencing the amplification products obtained (Takagaki et al., 1989); Asarnow et al., 1989). This powerful method is not without artifacts. Setting aside altogether the problems associated with quantification, it seems, for example, risky to deduce from two amplifications carried out with two different pairs of primers (V1, C) and (V2, C) for example, a preferential utilization of one segment relative to the other in the population under study (Rajasekar et al., 1990). In the current state of the art, it is difficult to determine by this method the degree of utilization of the different V segments. Moreover, cloning of the amplification products for the purpose of determining their sequence can also generate artifacts. For example, a certain proportion of these products are, in fact, heteroduplexes (if the amplified population is heterogeneous), for which it cannot be predicted how it will be "repaired" after transformation of the bacterium (Abastado et al., 1984, 1987).

A recent improvement is amplification according to the anchored PCR technique, which consists in carrying out the amplification of a heterogeneous population of complementary DNA using a single pair of primers, one hybridizing in the constant region C, the other with an identical sequence added at the 3' end of all the complementary DNA strands. It may hence be hoped that the amplification yield will not depend on the V segment used in the rearrangement.

Recently, a fairly sensitive method, enabling the degree of utilization of the different V segments in a population of heterogeneous transcripts to be evaluated, has been developed (Okada et Weissman, 1989; Singer et al., 1990). This accurate and reproducible method has the advantage of being conceptually simple, and hence of introducing little bias. However, it does not enable the V utilization and the J utilization to be defined simultaneously, nor does it enable it to be determined whether the transcript visualized is in frame.

Concomitantly with amplification from polyclonal populations, another widely used approach has consisted in constructing banks of hybridomas or of clonal T lines, and then characterizing at molecular level the antibodies or T receptors expressed. This method is obviously difficult to carry out on a large scale. It introduces biases which are difficult to evaluate during the steps of fusion or cloning, but is the only current technique that enables the sequence of both chains of a T receptor to be determined simultaneously, or a repertoire of a known specificity to be determined.

It should be noted that the methods mentioned above all characterize the repertoire from the messenger RNA and not from the protein, so that any post-transcriptional control is not known. The use of monoclonal antibodies and of flow cytofluorometry enables the repertoire to be analyzed at the level of the receptor itself, and gives simultaneously a large amount of information about the phenotype of the cells under study. However, this method is rather insensitive and, most particularly, does not enable the repertoire to be studied in detail since it is impossible, in the absence of reagents, to gain access to the junctional diversity of the repertoire. Furthermore, it requires the availability of a large battery of well-characterized monoclonal antibodies.

SUMMARY OF THE INVENTION

The subject of the present invention is, more especially, a method which enables an individual's immune repertoire to be described, and which can be readily automated, takes into account a very large number of parameters and is without the biases of the methods described previously.

More specifically, the present invention relates to a method for describing the repertoires of antibodies (Ab) and of T-cell receptors (TcR) of an individual's immune system, characterized in that:

starting with a biological sample, reverse transcription of the mRNA which it contains is performed, on the transcription product, or directly on the DNA extracted from the sample, separate amplifications are then performed by a PCR type method for each primer pair V,C, V corresponding to a variable segment of the repertoire in question and C hybridizing with the constant segment of the repertoire under study, on each of these amplification products, an elongation step is performed for each J segment of the repertoire, using a labelled oligonucleotide specific to this J segment as primer and the amplification product as template, for each elongation product corresponding to a triplet (V,C)J thereby obtained, the size of the different elongation products is revealed, to within one nucleotide, by the methods generally used for the determination of DNA sequences, the description of the repertoires corresponding, for each element of the repertoire, to a V,C,J triplet and to the size of the element.

An alternative consists in extracting the DNA from the biological sample and carrying out the amplification on the denatured DNA, using the fact that productive rearrangements bring together the variable segment and the constant region, so that only the variable segments used actually serve in the amplification.

The method according to the invention may be used either for describing one of the three repertoires, or else all three or only two of them. In what follows, the γδT repertoire will be described in particular, but the same methodology may be used for the αβT repertoire and immunoglobulins.

"Description of the repertoire" is understood to denote both a statement in the form of a two- or three-dimensional table, and a graphic representation and/or reproductions of gel, for example.

In effect, one of the values of the present invention is to be able to compare these repertoires, in particular, with typical repertoire statements capable of being associated with particular physiologies or pathologies, or alternatively to monitor the changes in these repertoires in the onset and/or progression of certain diseases such as some cancers, autoimmune diseases or AIDS. For example, during the immune reaction which occurs in at least a few types of cancer, rapid detection of tumor-infiltrating lymphocytes (TIL), and observation of the changes therein as well as in the remainder of the repertoire during a treatment by immunotherapy could prove an advantageous approach. It is possible to envisage applying the power of the method to the study of the changes in the repertoire during the development of an autoimmune disease. It is known, in effect, that, in many autoimmune diseases, the T lymphocytes occupy a position of key importance. Were strict correlations to be observed, following studies carried out in the few available animal models, between certain of these pathologies and a repertoire statement or succession of repertoire statements measured according to the method presented, it could then be fully envisaged that a predictive value would be given to this method of analysis, and consequently a value of earlier diagnosis than the tests currently available. This method may hence become a powerful investigative and analytical tool for the study and monitoring of the immune system.

The principles of the methodologies employed in this method are known.

Thus, when the sample is taken from the patient, the RNA (or DNA) will be prepared by known methods which may depend on the nature of the sample (peripheral blood or biopsy, for example).

The synthesis of complementary DNA by reverse transcription is known, as is the method enabling only the messenger mRNA present in this total RNA to be transcribed, by means of a poly(T) primer.

The amplification may be carried out by a PCR type method, that is to say by the PCR method or by one of its many variants.

The method is preferably carried out by PCR (polymerase chain reaction) and without the addition of any radioactive, colored or fluorescent tracer. The DNA is amplified, it being possible for the latter to originate either from a blood sample or from another sample or biopsy; however, the initial sample must contain a sufficiently large number of cells for the subsequent results to be statistically significant. Amplification begins with a reverse transcription step (or from the DNA extracted from the cells in the sample). After this, the sample is divided and separate amplification reactions, equal in number to the number of oligonucleotide pairs (V,C), are performed.

Each of the samples is then subdivided so as to carry out, for each of them, so-called elongation or "run-off" reactions equal in number to the number of J segments. To perform these reactions, oligonucleotides specific to these J segments are used, which oligonucleotides are labelled this time either with a radioactive tracer or, more advantageously, with a fluorophor or by other methods. In the "run-off" reaction, the polymerase recopies up to the end the segments amplified from the J oligonucleotide. If these are heterogeneous in length, a set of molecules labelled at their J end, and whose size can be measured accurately, is hence obtained.

This size measurement may be carried out on conventional DNA sequencing gels if a radioactive labelling has been performed or, advantageously, with an automatic sequencer, in particular one capable of detecting fluorophors. The apparatus is hence used only to measure the lengths and the intensity of the elongation products. Naturally, since there are four commercial fluorophors of different "colors", the products of four different reactions employing the different fluorophors may be mixed, as is done in DNA sequence determinations, but for completely different reasons. For example, it may be especially useful to mix the products of homologous reactions carried out on a control sample, and which are labelled with a given color, with those of three samples under study. In this way, a direct comparison is obtained between the samples and the control, but other experimental designs are possible. Some commercial apparatuses carry out an analysis of the four colors in 24 lanes simultaneously (equivalent to 96 samples). The analysis takes a few hours and the results are computerized.

By the use of a sequencer, it is possible to simplify the reading of the autoradiograms in the conventional sequence, which is lengthy. In the specific case described in the example, it is necessary to read each experiment and to memorize and interpret more than 1,000 elements. In the case of an automatic sequencer, the information is immediately stored, and the use of existing software, as well as of a software written in the context of the invention, enables the matrix of results to be obtained.

It will be noted that the practical problems are still more considerable for the αβ repertoire of the mouse, where analysis of some 60,000 elements is involved. The problem of the β repertoire is completely soluble according to the strategy adopted for the γ and δ repertoires. The problem of the α repertoire is arduous (5,000 samples to be analyzed for each repertoire), but simplifying strategies may be developed. The same applies to the antibody repertoires and the human repertoires.

Among apparatuses which can be readily adapted, the model 373A sequencer marketed by the company Applied Biosystems and related models should be mentioned.

By means of the software developed in the context of the invention, the data are organized either in a three-dimensional representation (genetic elements in a plane, length in the height), or in a two-dimensional table. This representation is preferable in that it makes it possible, in a matrix of dots, to represent the abundance of the reaction product (for example, the dot is darker or lighter according to the intensity of the band detected by the sequencer) and then to compare two matrices readily (two different repertoires, two statements of the same repertoire, and the like).

A possible improvement consists in introducing a fourth parameter which enables the repertoire to be analyzed still more finely. It should be recalled that this notion of resolution is of paramount importance if it is desired to be able to analyze changes in the current repertoire. In effect, the larger the number of parameters of measurement, the greater the resolution and the higher the chances of being able to pick up fine variations in the repertoire. This fourth parameter provides access, like the third, to the junctional diversity. It involves applying to the "run-off" products an electrophoresis method carried out in a gradient of temperature or of any other denaturing factor, so that products of the same size are separated according to their greater or lesser homology with a fixed probe (Riesner et al., 1989). What is sought is hence an indirect access to the sequence of the variable regions. Experiments are in progress employing the genes rearranged in hybridomas as probe.

The examples below are designed to demonstrate other advantages and features of the present invention.

DESCRIPTION OF THE FIGURES

In the attached Figures.

2A and 2B: B10.A mice immunized with pigeon cytochrome C.

1=unimmunized

2=after primary immunization

3=restimulation in vitro after primary immunization.

2C: C3H mice immunized with pigeon cytochrome C.

4, 5, 6=three different unimmunized mice

7=restimulation in vitro after primary immunization of a group of mice, the values appearing at right or left of the Figures correspond to the size (in nucleotides) of the elongated products obtained for a productive Vβ-Jβ combination.

DESCRIPTION OF A PREFERRED EMBODIMENT

Materials and methods

Oligonucleotides

The oligonucleotides used were synthesized on a 381A DNA Synthesier (Applied Biosystems) automated apparatus. Uncoupling from the column and unblocking of the phosphate functions (protected by a beta-cyanoethyl group)

are performed by injecting 1.5 ml of 28% ammonia solution into the column at the rate of 0.5 ml per 30 min. The eluate is incubated for 12 hours at 56° C. in order to deprotect the bases of the oligonucleotide (removal of the benzoyl and isobutyryl groups). After lyophilization, the oligonucleotide is resuspended in water at a concentration of 50 µM.

Mice, cells

Mice: All the strains used (Balb/c, Balb/b, DBA/2, CB 20, SJL and C3H/He) originate from the animal house of the Pasteur Institute. When matings were carried out, the first day of gestation, the day on which the vaginal plug is detected, is referred to as day 0.

Cells: The hybridomas used (S15, T14, T16, T18) result from the fusion of thymocytes of an adult C3H/He mouse with the partner BW5147$\alpha^-\beta^-$ (mutant of the AKR thymoma BW5147, no longer expressing the $\alpha\beta$ receptor.

Preparation of RNA

The RNA of tissues and cells in culture was prepared according to three different methods.

First method, used for preparing the RNA of cells in culture: the cells are centrifuged; the pellet obtained is resuspended in 10 ml of 10 mM NaCl/$CH_3$COONa pH 5, 1% SDS solution. After incubation for 2 min at 4° C., 10 ml of an unbuffered phenol solution at 65° C. are added. The mixture is stirred vigorously for 5 min; after centrifugation for 10 min at 3,000 rpm, the aqueous phase is withdrawn and remixed with one volume of chloroform/ isoamyl alcohol. After centrifugation, the RNA contained in the aqueous phase is precipitated by adding 0.1 volume of 3M sodium acetate pH 5.2 and two volumes of ethanol.

Second method, termed AGPC (acid guanidinium thiocyanate-phenol-chloroform) method: usable equally well for preparing the RNA of a cell pellet or of an organ, this method makes it possible to avoid in very large measure the degradation of ribonucleic acids which is liable to occur once cells are lysed. However, traces of DNA persist in the preparation, and may be troublesome in some applications.

The third method eliminates this contamination with DNA by exploiting the difference in density between ribo- and deoxyribonucleic acids. The separation of these two species is carried out by ultracentrifugation of the lysate in the presence of a discontinuous CsCl gradient: the DNA is retained at the interface of the gradient, while the denser RNA precipitates. This method hence makes it possible to recover both the RNA and the DNA of a tissue or a cell pellet. Briefly, a 4M solution of guanidine thiocyanate is prepared, containing 0.5% of Na N-laurylsarcosine, 25 mM EDTA, 0.13% of antifoam A. The CsCl gradient is composed of 3 ml of a 5.7M CsCl, 25 mM Na acetate pH 5.2, 10 mM EDTA solution and 0.7 ml of a 2.4M CsCl, 25 mM Na acetate pH 5.2, 10 mM EDTA solution. The tissue is ground in 7 ml of the 4M guanidine thiocyanate solution using a Potter homogenizer, and the lysate obtained is centrifuged for 10 min at 8,000 rpm in an HB-4 rotor to remove solid particles. The supernatant is deposited gently on the cushion of CsCl: the whole is centrifuged for 24 hours in an SW 41 rotor at 30,000 rpm at 20° C. The liquid phase is then removed (during this step the DNA located at the interface may be recovered), and the pellet is resuspended in 500 µl of water and precipitated at $-20°$ C. by adding 1 ml of ethanol and 50 µl of 3M Na acetate pH 5.2.

Preparation of complementary DNA

Synthesis of the complementary DNA is carried out from the total RNA prepared according to one of the three methods described above. The buffer used is the same as that of the PCR amplification step (Cetus buffer). In effect, the different buffers proposed did not prove to have substantially greater efficacy (comparison by measurement of the incorporation of $^{32}$P-labelled dCTP); in contrast, the $Mg_2^+$ concentration of these buffers does not permit PCR amplification to be carried out without a further intermediate step. The oligonucleotide used as primer of the polymerization of the complementary DNA strand is a poly-dT 15-mer. Briefly, 10 µg of total RNA, when the latter originates from an adult mouse organ, or the RNA of $10^5$ cells originating from a culture or from a fetal thymus, are incubated for 10 min at 70° C. in 50 µl of a 50 mM KCl, 10 mM Tris-HCl pH 8.2, 1.5 mM $MgCl_2$, 0.01% gelatin, 0.1 mM EDTA, 5 µM pdT(15), 0.2 mM dNTP solution. Then, after 5 min on ice, 5 units of AMV RT (Promega or Boehringer) are added, as well as 34 units of RNasin (Pharmacia); the mixture is incubated for 1 h at 43° C. and brought to 100° C. for 5 min.

Amplification by the PCR technique

The amplifications were carried out on Perkin Elmer Cetus and Prem automated equipment according to the technique described (Saiki et al., 1988).

To amplify complementary DNA, the protocol used was as follows: 5 µl of the solution prepared above are amplified in 50 or 100 µl of a solution comprising 50 mM KCl, 10 mM Tris-HCl pH 8.2, 0.01% gelatin, 0.2 µM each of the two oligonucleotides used, 2 u per 100 µl of Taq Polymerase (Beckman), 200 µM each of the nucleotides dATP, dGTP, dCTP and dTTP. The $Mg^{2+}$ ion concentration used varies from 2 to 2.5 mM. The mixture is covered with 50 µl of mineral oil, heated to 80° C. for 10 min, amplified by 40 cycles (1 min at 94° C., 1 min at 60° C., 1 min at 72° C.) and then incubated for 10 min at 72° C.

Among the parameters which enable the background of the method to be reduced, the use of optimal concentrations of magnesium ions in the amplification or elongation steps must be mentioned; thus, between 1 and 3 mM magnesium ions will preferably be used.

Labelling of primers, elongation by "run-off"

The J primers used for carrying out the "run-off" step were radiolabelled beforehand by phosphorylation of the 5' end using a [$^{32}$P]phosphate. The protocol is as follows: 100 pmol of the oligonucleotide are incubated in 10 µl for 30 min at 37° C. in the amplification buffer at a concentration of 2.5 mM $Mg^{2+}$ in the presence of 40 µCi of [$^{32}$P]-ATP (equivalent to 12 pmol) and 3 units of T4 polynucleotide kinase. The enzyme is then inactivated by bringing the mixture to 70° C. for 10 min.

Elongation by "run-off" from the labelled J primers is carried out under the following conditions. 1 µl of the mixture amplified above is diluted in 10 µl of a solution identical to that which was used for the amplification (amplification buffer with the optimal $Mg^{2+}$ concentration (2 to 2.5 mM), 200 µM each of the dNTPs, 0.2 u of Taq Polymerase), to which the labelled J primer at a concentration of 1 µM is added (the J primer is hence [lacuna] an at least 5-fold excess relative to the other primers V and C supplied by the μl of the amplified mixture). The "run-off" reaction consists of 3 min at 94° C., 1 min at 60° C. followed by 15 min at 72° C.

Electrophoresis

Analysis of the amplification products and the sequences is carried out by electrophoresis on 6% polyacrylamide gel (crosslinking: 1 g of bisacrylamide to 19 g of acrylamide) of thickness 400 μm, in TBE buffer (Maniatis et al., 1982) under denaturing conditions (95% formamide, 20 mM EDTA, 0.25% bromophenol blue, 0.25% xylene cyanole), and incubated for 10 min at 80° C. Migration is carried out in TBE buffer under an electric field of 4,000 Vm$^{-1}$, for 2 h or 4 h for sequence analysis, and 5 to 6 h for analysis of amplification products.

Example 1

Study of the genetic diversity of the γ chain of the T receptor in the mouse

Principle of the method

For each variable chain (Vα, Vβ, Vγ or Vδ for the αβ- or γδT receptors), the specific oligonucleotides are synthesized and enable the cDNA copies of the messenger RNAs to be amplified separately. The table below gives the list of oligonucleotides used in the following analysis. The transcripts corresponding to the variable regions Vγ1, Vγ2 ... Vγ7 are amplified separately, as are those corresponding to Vδ1, Vδ2 ... Vδ9. For each amplification product, a reaction specific to the J segments is carried out. Finally, the size of the products is measured on a sequencing gel. This enables the messenger RNAs to be broken down according to the length of the variable region (N region in particular), which can vary from 10 to 20 nucleotides approximately. In addition, it is possible to identify the messenger RNAs which are out-of-frame for translation into protein. In summary, a sample is parametrized (1) for the use of the V chains, (2) for the use of the J segments and (3) for size.

The genetic diversity, for the γδT receptors of the mouse, originates from the matching up of 15 genetic elements for the γ chain of the receptor and 11 elements of the δ chain. During recombinations which give rise to active genes of structure V-D-J-C, various mechanisms operate at the junctions of certain recombined segments so that the length of the active gene is variable within limits which are from 0 to 20 nucleotides approximately for the Vγ-Jγ-Cγ genes and from 0 to 50 nucleotides approximately for the Vδ-Jδ-Cδ genes.

The repertoire of the γδT receptor was parametrized by determination:

of the V,J and C segments which are used, of the length of the rearranged gene.

It is seen in Table 1 that this represents more than about a thousand measurements for the γδT receptors. In the case of the αβT receptors, more than 50,000 measurements are involved.

Experimental method

For the repertoire of γδT receptors of the mouse, the following are synthesized:

7 oligonucleotides specific to Vγ chains, 3 oligonucleotides specific to Jγ chains, 4 oligonucleotides specific to Cγ chains, 9 oligonucleotides specific to Vδ chains, 2 oligonucleotides specific to Jδ chains, 1 oligonucleotide specific to the Cδ chain.

The methods of determination of the primers are known, especially where strong homologies exist between sequences which it is intended to distinguish, for example Vγ1, Vγ2 and Vγ3.

Attached Table 2 gives the list of oligonucleotides used.

Figure 1:
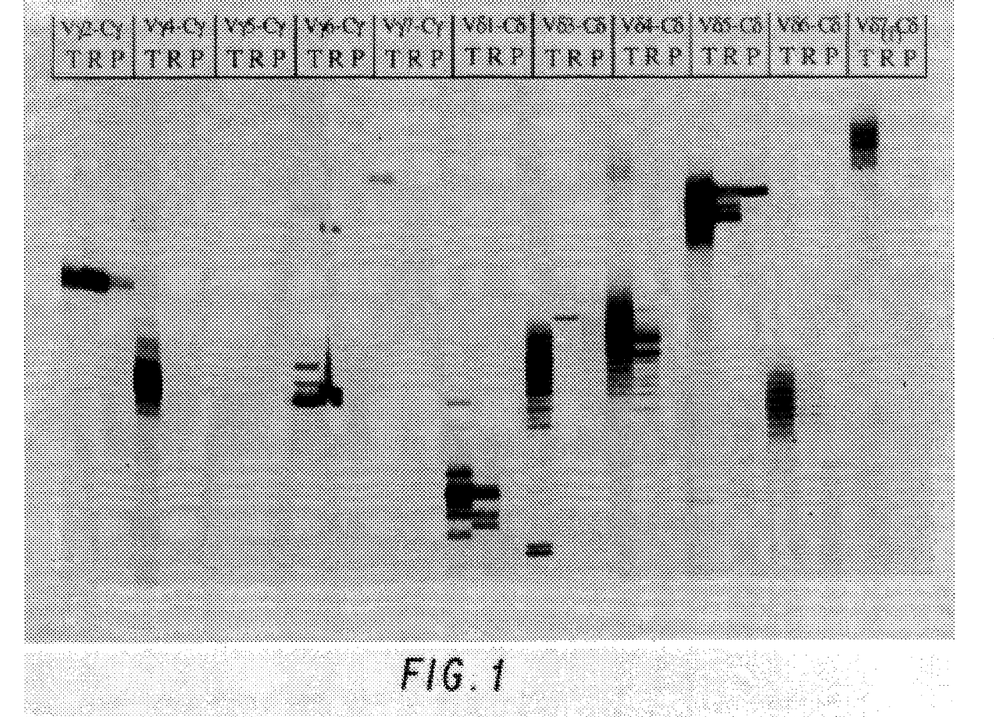
FIG. 1 shows a portion of the γδT repertoire in the thymus (T) and spleen (S) of an adult Balb/c mouse and the placenta (P) of an F1 mouse (C3H×C57/B16)

The results obtained are recorded in FIG. 1 without the J utilization.

TABLE 1

| | Immunoglobulin | | | αβ Receptor (1) | | γδ Receptor (2) | |
|---|---|---|---|---|---|---|---|
| | V$_H$ Chain | V$_κ$ Chain | V$_γ$ Chain | α Chain | β Chain | γ Chain | δ Chain |
| Mouse repertoires | | | | | | | |
| V segments | 250–1000 | 250 | 2 | 100 | 25 | 7 | 10 |
| D segments | 12 | 0 | 0 | 0 | 2 | 0 | 2 |
| J segments | 4 + 1 | 4 + 1 | 4 | 50 | 12 | 3 | 2 |
| C regions | 8 isotypes | 1 | 4 | 1 | 2 | 4 | 1 |
| Total div. (3) | | 10$^{11}$ | | | 10$^{15}$ | | 10$^{18}$ |
| Human repertoires (4) | | | | | | | |
| V segments | 100–200 | 80 | | 60 | 80 | 8 + 6 | 4 |
| D segments | 4 | 0 | 0 | 0 | 2 | 0 | 2 |
| J segments | 6 + 3 | 5 | 6 | 50 | 13 | 5 | 3 |
| C regions | 10 isotypes | 1 | 6 | 1 | 2 | 2 | 1 |

(1) Wilson et al. (1988)
(2) Raulet (1989)
(3) Davis and Bjorkman (1988)
(4) Meindl et al. (1990)

TABLE 2

| | |
|---|---|
| $V_\gamma 1$: (SEQ ID NO: 1) | AGTTTGAGTATCTAATATATGTCT |
| $V_\gamma 2$: (SEQ ID NO: 2) | ACGACCCTTAGGAGGGAAGC |
| $V_\gamma 3$: (SEQ ID NO: 3) | TTGAGTATCTAATATATGTCGAG |
| $V_\gamma 2$: (SEQ ID NO: 4) | CGGCAAAAAACAAATCAACAG |
| $V_\gamma 4$: (SEQ ID NO: 5) | TGTCCTTGCAACCCCTACCC |
| $V_\gamma 5$: (SEQ ID NO: 6) | TGTGCACTGGTACCAACTGA |
| $V_\gamma 6$: (SEQ ID NO: 7) | GGAATTCAAAAGAAAACATTGTCT |
| $V_\gamma 7$: (SEQ ID NO: 8) | AAGCTAGAGGGGTCCTCTGC |
| $J_\gamma 1$: (SEQ ID NO: 9) | CTGCAAATACCTTGTGAAAA |
| $J_\gamma 2$: (SEQ ID NO: 10) | CTGCAAATACCTTGTGAAAG |
| $J_\gamma 4$: (SEQ ID NO: 11) | GAATTACTACGAGCTTTGTC |
| $C_\gamma 1$: (SEQ ID NO: 12) | TTTCAGCAACAGAAGGAAGG |
| $C_\gamma 2$: (SEQ ID NO: 13) | TCCAGGATAGTATTGCCATT |
| $C_\gamma 3$: (SEQ ID NO: 14) | GGAAATGTCTGCATCAAGCT |
| $C_\gamma 4$: (SEQ ID NO: 15) | GCTTGGGAGAAAAGTCTGAG |
| pan-$C_\gamma$: (SEQ ID NO: 16) | CTTATGGAGATTTGTTTCAGC |
| $V\delta 1$: (SEQ ID NO: 17) | GGAATTCAGAAGGCAACAATGAAAG |
| $V\delta 2$: (SEQ ID NO: 18) | GTTCCCYGCAGATCCAAGCC |
| $V\delta 3$: (SEQ ID NO: 19) | TTCCTGGCTATTGCCTCTGAC |
| $V\delta 4$: (SEQ ID NO: 20) | CCGCTTCTGTGTGAACTTCC |
| $V\delta 5$: (SEQ ID NO: 21) | CAGATCCTTGCAGTTCATCC |
| $V\delta 6$: (SEQ ID NO: 22) | TCAAGTCCATCAGCCTTGTC |
| $V\delta 7$-R$^{(2)}$: (SEQ ID NO: 23) | GAAAGCTTCAGTGCAAGAGTC |
| $V\delta 7$-T: (SEQ ID NO: 24) | CGCAGAGCTGCAGTGTAAGT |
| $V\delta 8$: (SEQ ID NO: 25) | GCTACAGCACCCTGCACATC |
| $J\delta 1$: (SEQ ID NO: 26) | TCCACAGTCACTTGGGTTCC |
| $J\delta 2$: (SEQ ID NO: 27) | TCCACAAAGAGCTCTATGCC |
| $C\delta$: (SEQ ID NO: 28) | CGAATTCCACAATCTTCTTG |

(1) The nomenclatures used are that of Heilig & Tonegawa (1986) for the γ locus and that of Raulet (1989) for the δ locus. The choice of a portion of the oligonucleotides originates directly from Takagaki et al. (1989 b).

(2) Vδ7-R is the oligonucleotide specific to the variable segment Vδ7 referenced in Raulet (1989); Vδ7-T is the oligonucleotide specific to the variable segment Vδ7 referenced in Takagaki et al. (1989 a).

Example 2

Analysis of the genetic diversity of the αβT receptor

The genetic diversity of the β chain of the T receptor on lymph nodes of B10.A mice, after immunization with pigeon cytochrome C, constitutes a well-documented reference system. In particular, according to published studies, it is known that the β chain of 75 to 80% of the clones isolated after immunization and restimulation in vitro with the antigen is composed of the rearrangement Vβ3-Jβ1.2-Cβ.

A sample of messenger RNA originating from draining lymph nodes of immunized or unimmunized mice was converted into cDNA. This was amplified by PCR (polymerase chain reaction) with an oligonucleotide pair located, on the one hand in one of the Vβ variable regions, and on the other hand in the constant region. This operation was repeated for each Vβ region (numbering about twenty). After this, each amplification reaction, divided into 12 samples (one for each Jβ), served as a template for an elongation cycle with one of the 12 radiolabelled Jβ.

Figure 2A:
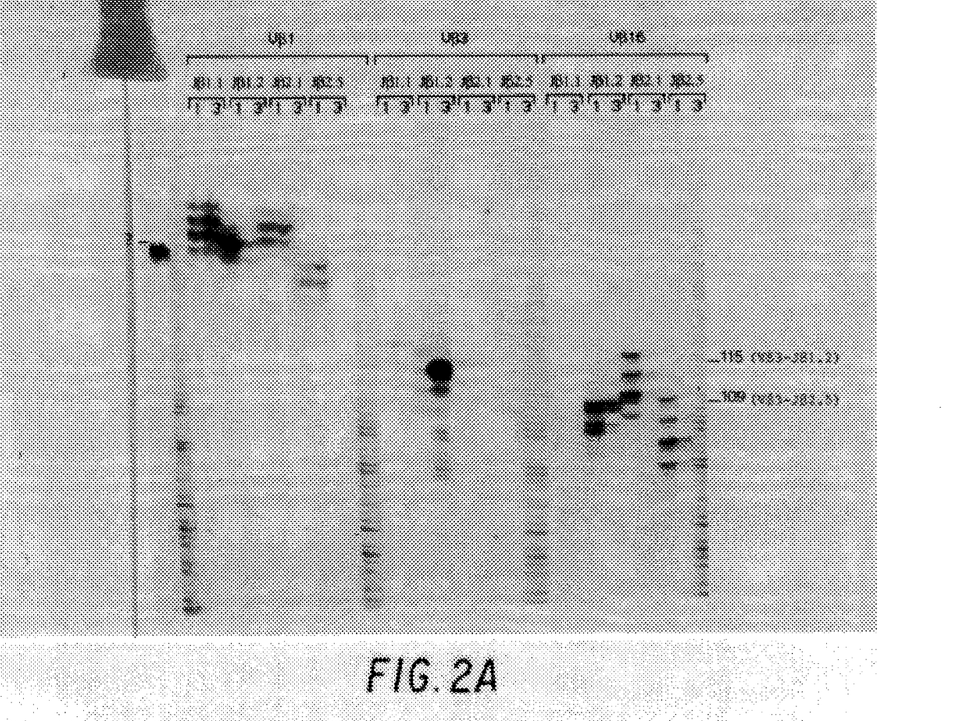
FIGS. 2A–2C show the analysis on denaturing gel of the elongation products obtained with different Jβ primers on the DNA extracted from lymph nodes, amplified by PCR with primers specific to the Vβ and Cβ segments.
Figure 2B:
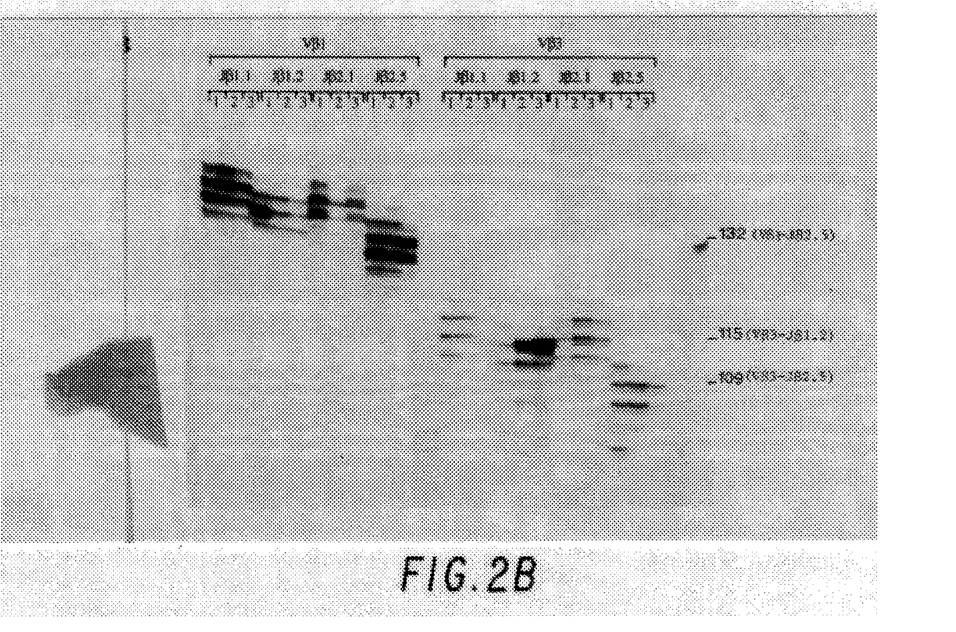

Attached FIGS. 2A–2C illustrates a part of the results obtained for the pairs Vβ1-Vβ3 and Vβ16-Cβ, reanalyzed with four different Jβ including Jβ1.2, on B10.A mice (H-2a) in two independent experiments (FIGS. 2A and 2B). In FIG. 2A, for the pair Vβ3-Jβ1.2, a preponderant band is seen to appear in the T cells of the lymph nodes restimulated in vitro with pigeon cytochrome C (FIG. 2A, track 3). The size of the fragments of which this band is composed is in agreement with the expected results (115 nucleotides for Vβ3-Jβ1.2). These results are reproducible from one experiment to another (FIG. 2B) and, in addition, indicate that the preponderance of the rearrangement Vβ3-Jβ1.2 is already detectable after the first immunization (FIG. 2B, Jβ1.2, track 2).

Figure 2C:
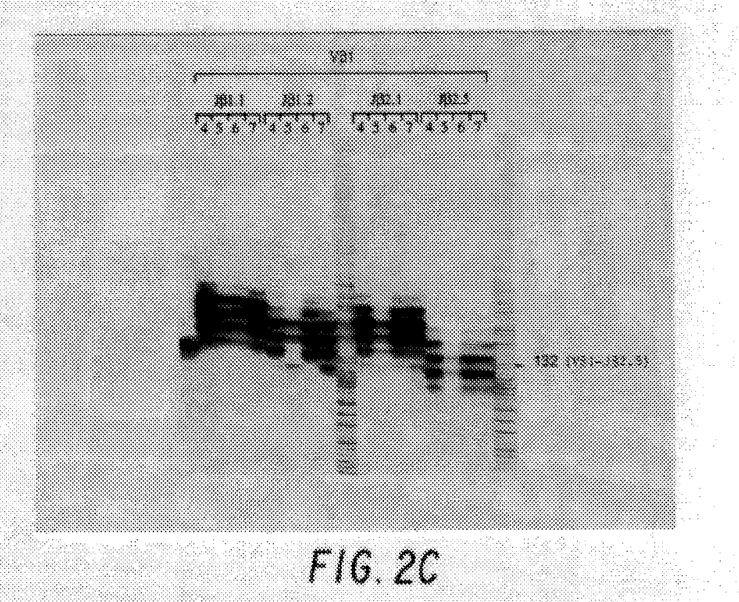

It is not ruled out to be able to carry out this type of analysis on one and the same mouse so as to avoid the problem of the minimal variations existing from one mouse to another, as illustrated in FIG. 2C (tracks 4 to 6).

BIBLIOGRAPHIC REFERENCES

ABASTADO et al. (1984). Proc. Natl. Acad. Sci. USA 81, 5792–5796

ABASTADO et al. (1987). Proc. Natl. Acad. Sci. USA 84, 6496–6500

ASARNOW et al. (1989). Nature 341, 60–62

DAVIS and BJORKMAN (1988). Nature 334, 395–402

MANIATIS et al. (1982). Molecular Cloning: Laboratory Manual. Cold Spring Harbor Laboratory MEINDL et al. (1990). Eur. J. Immunol. 20, 1855–1863

OKADA et WEISSMAN (1989). J. Exp. Med. 169, 1703–1719

RAJASEKAR et al. (1990). Proc. Natl. Acad. Sci. USA 87, 1767–1771

RAULET (1989). Ann. Rev. Immunol. 7, 175–207

RIESNER et al. (1989). Electrophoresis 10, 377–389

SAIKI et al. (1988). Science 239, 487–491

SINGER et al. (1990). EMBO J. (in press)

TAKAGAKI et al. (1989). Nature 339, 712–714

TONEGAWA (1983). Nature 302, 575–581

WILSON et al. (1988). Immunological Reviews 101, 149–172

We claim:

1. A method for describing the repertoires of antibodies (Ab) and of T-cell receptors (TcR) of an individual's immune system, comprising the steps of:
   a) obtaining a biological sample containing mRNA encoding said antibodies and T-cell receptors which contain different variable (V) and constant (C) segments,
   b) reverse transcribing the mRNA to obtain a transcription product,
   c) performing separate amplifications on the transcription product to form amplification products using a DNA enzymatic amplification method and separate primer pairs V,C, for each different V and C segment of the repertoire under study,
   d) performing an elongation step on each amplification product for each J segment of the repertoire to form different elongation products, using as primer an oligonucleotide specific to said J segment, said oligonucleotide comprising a label,
   e) revealing signals representing the molecular size of the different elongation products for each elongation product corresponding to a triplet (V,C) J thereby obtained, wherein each signal has a particular intensity, and
   f) obtaining a description of the repertoires corresponding, for each segment of the repertoires, to a VCJ triplet and to the size of the segment.

2. A method according to claim 1, wherein in step e) the sizes of the elongation products are revealed by electrophoresis of said elongation products and detection of said labeled oligonucleotide.

3. A method according to claim 1 wherein in step d) the label is radioactive, colorimetric or fluorescent.

4. Method according to claim 1 wherein the steps are performed in the presence of 1 to 3 mM $Mg^{2+}$ ion.

5. Method according to claim 1 wherein the intensity of each signal of molecular size is measured in order to obtain a quantitative measurement of the extent of the corresponding sequence.

6. Method according to claim 5, wherein the intensity of each signal is evaluated relative to an internal standard.

7. Method according to claim 1 wherein products of the same molecular size are separated in accordance with their greater or lesser affinity for a fixed probe.

8. Method according to claim 7, wherein step e) is performed using electrophoresis with a gradient of temperature or of any other denaturing agent.

9. Method according to claim 1 wherein an automatic sequencing apparatus is used to reveal and describe the sizes of the elongation products.

10. A method for describing the repertoires of antibodies (Ab) and of T-cell receptors (TcR) of an individual's immune system comprising the steps of:
    a) obtaining a biological sample containing mRNA encoding said antibodies and T-cell receptors which contain different variable (V) and constant (C) segments,
    b) isolating DNA from said biological sample,
    c) performing separate amplifications on said DNA by an enzymatic amplification method and separate primer pairs V,C, for each different V and C segment of the repertoire under study,
    d) performing an elongation step on each amplification product for each J segment of the repertoire to form different elongation products, using as primer an oligonucleotide specific to said J segment, said oligonucleotide comprising a label,
    e) revealing signals representing the molecular size of the different elongation products for each elongation product corresponding to a triplet (V,C) J thereby obtained, wherein each signal has a particular intensity, and
    f) obtaining a description of the repertoires corresponding, for each segment of the repertoire, to a VCJ triplet and to the size of the segment.

* * * * *

SEQUENCE LISTING ( 1 ) GENERAL INFORMATION:

( i i i ) NUMBER OF SEQUENCES: 28

( 2 ) INFORMATION FOR SEQ ID NO:1:

( i ) SEQUENCE CHARACTERISTICS:
        ( A ) LENGTH: 24 base pairs
        ( B ) TYPE: nucleic acid
        ( C ) STRANDEDNESS: unknown
        ( D ) TOPOLOGY: unknown     ( i i ) MOLECULE TYPE: DNA (genomic)

( x i ) SEQUENCE DESCRIPTION: SEQ ID NO:1:

AGTTTGAGTA TCTAATATAT GTCT    24

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: unknown
        ( D ) TOPOLOGY: unknown     ( i i ) MOLECULE TYPE: DNA (genomic)

( x i ) SEQUENCE DESCRIPTION: SEQ ID NO:2:

ACGACCCTTA GGAGGGAAGC    20

( 2 ) INFORMATION FOR SEQ ID NO:3:

( i ) SEQUENCE CHARACTERISTICS:
        ( A ) LENGTH: 23 base pairs
        ( B ) TYPE: nucleic acid
        ( C ) STRANDEDNESS: unknown
        ( D ) TOPOLOGY: unknown     ( i i ) MOLECULE TYPE: DNA (genomic)

( x i ) SEQUENCE DESCRIPTION: SEQ ID NO:3:

TTGAGTATCT AATATATGTC GAG    23

( 2 ) INFORMATION FOR SEQ ID NO:4:

( i ) SEQUENCE CHARACTERISTICS:
        ( A ) LENGTH: 21 base pairs
        ( B ) TYPE: nucleic acid
        ( C ) STRANDEDNESS: unknown
        ( D ) TOPOLOGY: unknown     ( i i ) MOLECULE TYPE: DNA (genomic)

( x i ) SEQUENCE DESCRIPTION: SEQ ID NO:4:

CGGCAAAAAA CAAATCAACA G    21

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: unknown
        ( D ) TOPOLOGY: unknown     ( i i ) MOLECULE TYPE: DNA (genomic)

( x i ) SEQUENCE DESCRIPTION: SEQ ID NO:5:

TGTCCTTGCA ACCCCTACCC                                                           20

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: unknown
        ( D ) TOPOLOGY: unknown     ( i i ) MOLECULE TYPE: DNA (genomic)

( x i ) SEQUENCE DESCRIPTION: SEQ ID NO:6:

TGTGCACTGG TACCAACTGA                                                           20

( 2 ) INFORMATION FOR SEQ ID NO:7:

( i ) SEQUENCE CHARACTERISTICS:
        ( A ) LENGTH: 24 base pairs
        ( B ) TYPE: nucleic acid
        ( C ) STRANDEDNESS: unknown
        ( D ) TOPOLOGY: unknown     ( i i ) MOLECULE TYPE: DNA (genomic)

( x i ) SEQUENCE DESCRIPTION: SEQ ID NO:7:

GGAATTCAAA AGAAAACATT GTCT                                                      24

( 2 ) INFORMATION FOR SEQ ID NO:8:

( i ) SEQUENCE CHARACTERISTICS:
        ( A ) LENGTH: 20 base pairs
        ( B ) TYPE: nucleic acid
        ( C ) STRANDEDNESS: unknown
        ( D ) TOPOLOGY: unknown     ( i i ) MOLECULE TYPE: DNA (genomic)

( x i ) SEQUENCE DESCRIPTION: SEQ ID NO:8:

AAGCTAGAGG GGTCCTCTGC                                                           20

( 2 ) INFORMATION FOR SEQ ID NO:9:

( i ) SEQUENCE CHARACTERISTICS:
        ( A ) LENGTH: 20 base pairs
        ( B ) TYPE: nucleic acid
        ( C ) STRANDEDNESS: unknown
        ( D ) TOPOLOGY: unknown     ( i i ) MOLECULE TYPE: DNA (genomic)

( x i ) SEQUENCE DESCRIPTION: SEQ ID NO:9:

CTGCAAATAC CTTGTGAAAA                                                           20

( 2 ) INFORMATION FOR SEQ ID NO:10:

( i ) SEQUENCE CHARACTERISTICS:
        ( A ) LENGTH: 20 base pairs
        ( B ) TYPE: nucleic acid
        ( C ) STRANDEDNESS: unknown
        ( D ) TOPOLOGY: unknown     ( i i ) MOLECULE TYPE: DNA (genomic)

( x i ) SEQUENCE DESCRIPTION: SEQ ID NO:10:

CTGCAAATAC CTTGTGAAAG                                                           20

( 2 ) INFORMATION FOR SEQ ID NO:11:

( i ) SEQUENCE CHARACTERISTICS:
  ( A ) LENGTH: 20 base pairs
  ( B ) TYPE: nucleic acid
  ( C ) STRANDEDNESS: unknown
  ( D ) TOPOLOGY: unknown ( i i ) MOLECULE TYPE: DNA (genomic)

( x i ) SEQUENCE DESCRIPTION: SEQ ID NO:11:

GAATTACTAC GAGCTTTGTC                    20

( 2 ) INFORMATION FOR SEQ ID NO:12:

( i ) SEQUENCE CHARACTERISTICS:
    ( A ) LENGTH: 20 base pairs
    ( B ) TYPE: nucleic acid
    ( C ) STRANDEDNESS: unknown
    ( D ) TOPOLOGY: unknown ( i i ) MOLECULE TYPE: DNA (genomic)

( x i ) SEQUENCE DESCRIPTION: SEQ ID NO:12:

TTTCAGCAAC AGAAGGAAGG                    20

( 2 ) INFORMATION FOR SEQ ID NO:13:

( i ) SEQUENCE CHARACTERISTICS:
    ( A ) LENGTH: 20 base pairs
    ( B ) TYPE: nucleic acid
    ( C ) STRANDEDNESS: unknown
    ( D ) TOPOLOGY: unknown ( i i ) MOLECULE TYPE: DNA (genomic)

( x i ) SEQUENCE DESCRIPTION: SEQ ID NO:13:

TCCAGGATAG TATTGCCATT                    20

( 2 ) INFORMATION FOR SEQ ID NO:14:

( i ) SEQUENCE CHARACTERISTICS:
    ( A ) LENGTH: 20 base pairs
    ( B ) TYPE: nucleic acid
    ( C ) STRANDEDNESS: unknown
    ( D ) TOPOLOGY: unknown ( i i ) MOLECULE TYPE: DNA (genomic)

( x i ) SEQUENCE DESCRIPTION: SEQ ID NO:14:

GGAAATGTCT GCATCAAGCT                    20

( 2 ) INFORMATION FOR SEQ ID NO:15:

( i ) SEQUENCE CHARACTERISTICS:
    ( A ) LENGTH: 20 base pairs
    ( B ) TYPE: nucleic acid
    ( C ) STRANDEDNESS: unknown
    ( D ) TOPOLOGY: unknown ( i i ) MOLECULE TYPE: DNA (genomic)

( x i ) SEQUENCE DESCRIPTION: SEQ ID NO:15:

GCTTGGGAGA AAAGTCTGAG                    20

( 2 ) INFORMATION FOR SEQ ID NO:16:

( i ) SEQUENCE CHARACTERISTICS:
    ( A ) LENGTH: 21 base pairs
    ( B ) TYPE: nucleic acid
    ( C ) STRANDEDNESS: unknown
    ( D ) TOPOLOGY: unknown (i i) MOLECULE TYPE: DNA (genomic)

(x i) SEQUENCE DESCRIPTION: SEQ ID NO:16:

CTTATGGAGA TTTGTTTCAG C  21

(2) INFORMATION FOR SEQ ID NO:17:

(i) SEQUENCE CHARACTERISTICS:
        (A) LENGTH: 25 base pairs
        (B) TYPE: nucleic acid
        (C) STRANDEDNESS: unknown
        (D) TOPOLOGY: unknown     (i i) MOLECULE TYPE: DNA (genomic)

(x i) SEQUENCE DESCRIPTION: SEQ ID NO:17:

GGAATTCAGA AGGCAACAAT GAAAG  25

(2) INFORMATION FOR SEQ ID NO:18:

(i) SEQUENCE CHARACTERISTICS:
        (A) LENGTH: 20 base pairs
        (B) TYPE: nucleic acid
        (C) STRANDEDNESS: unknown
        (D) TOPOLOGY: unknown     (i i) MOLECULE TYPE: DNA (genomic)

(x i) SEQUENCE DESCRIPTION: SEQ ID NO:18:

GTTCCC Y GCA GATCCAAGCC  20

(2) INFORMATION FOR SEQ ID NO:19:

(i) SEQUENCE CHARACTERISTICS:
        (A) LENGTH: 21 base pairs
        (B) TYPE: nucleic acid
        (C) STRANDEDNESS: unknown
        (D) TOPOLOGY: unknown     (i i) MOLECULE TYPE: DNA (genomic)

(x i) SEQUENCE DESCRIPTION: SEQ ID NO:19:

TTCCTGGCTA TTGCCTCTGA C  21

(2) INFORMATION FOR SEQ ID NO:20:

(i) SEQUENCE CHARACTERISTICS:
        (A) LENGTH: 20 base pairs
        (B) TYPE: nucleic acid
        (C) STRANDEDNESS: unknown
        (D) TOPOLOGY: unknown     (i i) MOLECULE TYPE: DNA (genomic)

(x i) SEQUENCE DESCRIPTION: SEQ ID NO:20:

CCGCTTCTGT GTGAACTTCC  20

(2) INFORMATION FOR SEQ ID NO:21:

(i) SEQUENCE CHARACTERISTICS:
        (A) LENGTH: 20 base pairs
        (B) TYPE: nucleic acid
        (C) STRANDEDNESS: unknown
        (D) TOPOLOGY: unknown     (i i) MOLECULE TYPE: DNA (genomic)

(x i) SEQUENCE DESCRIPTION: SEQ ID NO:21:

CAGATCCTTG CAGTTCATCC　　　　　　　　　　　　　　　　　　　　　　　　　　　　　　　20

( 2 ) INFORMATION FOR SEQ ID NO:22:

( i ) SEQUENCE CHARACTERISTICS:
    ( A ) LENGTH: 20 base pairs
    ( B ) TYPE: nucleic acid
    ( C ) STRANDEDNESS: unknown
    ( D ) TOPOLOGY: unknown   ( i i ) MOLECULE TYPE: DNA (genomic)

( x i ) SEQUENCE DESCRIPTION: SEQ ID NO:22:

TCAAGTCCAT CAGCCTTGTC　　　　　　　　　　　　　　　　　　　　　　　　　　　　　　　20

( 2 ) INFORMATION FOR SEQ ID NO:23:

( i ) SEQUENCE CHARACTERISTICS:
    ( A ) LENGTH: 21 base pairs
    ( B ) TYPE: nucleic acid
    ( C ) STRANDEDNESS: unknown
    ( D ) TOPOLOGY: unknown   ( i i ) MOLECULE TYPE: DNA (genomic)

( x i ) SEQUENCE DESCRIPTION: SEQ ID NO:23:

GAAAGCTTCA GTGCAAGAGT C　　　　　　　　　　　　　　　　　　　　　　　　　　　　　 21

( 2 ) INFORMATION FOR SEQ ID NO:24:

( i ) SEQUENCE CHARACTERISTICS:
    ( A ) LENGTH: 20 base pairs
    ( B ) TYPE: nucleic acid
    ( C ) STRANDEDNESS: unknown
    ( D ) TOPOLOGY: unknown   ( i i ) MOLECULE TYPE: DNA (genomic)

( x i ) SEQUENCE DESCRIPTION: SEQ ID NO:24:

CGCAGAGCTG CAGTGTAAGT　　　　　　　　　　　　　　　　　　　　　　　　　　　　　　　20

( 2 ) INFORMATION FOR SEQ ID NO:25:

( i ) SEQUENCE CHARACTERISTICS:
    ( A ) LENGTH: 20 base pairs
    ( B ) TYPE: nucleic acid
    ( C ) STRANDEDNESS: unknown
    ( D ) TOPOLOGY: unknown   ( i i ) MOLECULE TYPE: DNA (genomic)

( x i ) SEQUENCE DESCRIPTION: SEQ ID NO:25:

GCTACAGCAC CCTGCACATC　　　　　　　　　　　　　　　　　　　　　　　　　　　　　　　20

( 2 ) INFORMATION FOR SEQ ID NO:26:

( i ) SEQUENCE CHARACTERISTICS:
    ( A ) LENGTH: 20 base pairs
    ( B ) TYPE: nucleic acid
    ( C ) STRANDEDNESS: unknown
    ( D ) TOPOLOGY: unknown   ( i i ) MOLECULE TYPE: DNA (genomic)

( x i ) SEQUENCE DESCRIPTION: SEQ ID NO:26:

TCCACAGTCA CTTGGGTTCC　　　　　　　　　　　　　　　　　　　　　　　　　　　　　　　20

( 2 ) INFORMATION FOR SEQ ID NO:27:

(i) SEQUENCE CHARACTERISTICS:
   (A) LENGTH: 20 base pairs
   (B) TYPE: nucleic acid
   (C) STRANDEDNESS: unknown
   (D) TOPOLOGY: unknown (ii) MOLECULE TYPE: DNA (genomic)

(xi) SEQUENCE DESCRIPTION: SEQ ID NO:27:

TCCACAAAGA GCTCTATGCC                                           20

(2) INFORMATION FOR SEQ ID NO:28:

(i) SEQUENCE CHARACTERISTICS:
   (A) LENGTH: 20 base pairs
   (B) TYPE: nucleic acid
   (C) STRANDEDNESS: unknown
   (D) TOPOLOGY: unknown (ii) MOLECULE TYPE: DNA (genomic)

(xi) SEQUENCE DESCRIPTION: SEQ ID NO:28:

CGAATTCCAC AATCTTCTTG                                           20